US00PP09019P

United States Patent [19]

Perrino

[11] Patent Number: Plant 9,019

[45] Date of Patent: Dec. 20, 1994

[54] TULBAGHIA PLANT NAMED "PERTAYLOR"

[76] Inventor: Frank Perrino, 22231 De La Osa St., Woodland Hills, Calif. 91364

[21] Appl. No.: 157,639

[22] Filed: Nov. 24, 1993

[51] Int. Cl.[5] ..... A01H 5/00

[52] U.S. Cl. ..... Plt./68.1

[58] Field of Search ..... Plt. 68.1

*Primary Examiner*—James R. Feyrer

*Attorney, Agent, or Firm*—Christie, Parker & Hale

[57] ABSTRACT

A new variety of Tulbaghia which is a mutation of *Tulbaghia violacea* and produces flowers of near white coloration.

2 Drawing Sheets

BACKGROUND OF THE INVENTION

The present invention relates to a new and distinct variety of Tulbaghia which was discovered as a mutation in a controlled planting of *Tulbaghia violacea*. The varietal denomination of the new variety is 'Pertaylor.'

SUMMARY OF THE INVENTION

Among the novel characteristics possessed by the new variety which distinguishes it from its parent and other varieties of which I am aware are its attractive white flowers born on a plant similar to its parent. The production of white flowers distinguish 'Pertaylor' from *Tulbaghia violacea* which produces violet flowers. 'Pertaylor' is a bushy upright plant and may be cultivated for outdoor garden decoration. It is asexually reproducible by division and tissue culture.

Asexual reproduction of the new variety, by division, as performed in Los Angeles County, Calif., shows that the foregoing and other distingiushing characteristics come true to form and are transmitted through succeeding propagations.

BRIEF DESCRIPTION OF THE ILLUSTRATION

The accompanying illustrations show typical specimens of the vegetative growth and flowers of the new variety, including its distinguishing predominately white flower color, depicted in color as nearly true as it is reasonably possible to make the same in a color illustration of this character.

In one first photograph, a series of specimens are depicted which are approaching flowering stage, and which illustrate the foliage of the plant as well as the basally sheathed attachment of ligulate leaves. One specimen of the series depicted has bolted, forming a solitary scape bearing a flower.

The second photograph shows the top part of the terete scape composed of many flowers of star-like appearance on short pedicels in a loose scapose umbel. The unique, predominately white coloration of the flowers is shown to be white with violet lines or spots at the apex of the petal lobes of opening flowers; but with flowers otherwise substantially pure white in appearance.

DETAILED DESCRIPTION OF THE NEW VARIETY

The following is a detailed description of my new variety, with color terminology in accordance with The Royal Horticultural Society Color Chart (RHSCC). The terminology used in color descriptions herein refers to plate numbers in the aforementioned color chart, except where common terms of color definition are employed.

The horticultural observations described are from plants of the new variety grown outdoors in Los Angeles County. Phenotypic expression may vary with differences in conditions of light, soil and climate.

FLOWERS

The new variety bears its flowers on a simple leafless scape. Numerous pedicellate flowers are borne in a terminal umbel subtended by 2 spathe valves on medium strength, medium to long stems. Outdoors the plant blooms very freely during the summer with the flowers being numerous and pedicellate.

The pedicel is of short to average length, of slender to average caliper, and sometimes bending. It is almost entirely smooth. Pedicel color is between 137A and 144A.

The perianth is urn-shaped to almost salver-shaped and of average size and length for the species. There are 6 sub-equal spreading lobes. Lobe color is between pure white and 155D, often tipped with between 75A and 77C. As the flower ages, the tip color fades to near 155D.

The crown is rather fleshy at the throat and of shorter length than the lobes. At the point of attachment to the pedicel, the crown color is between 150C and 150D gradually dissipating to between pure white and 155D moving toward the lobes.

The general tonality of the flower is near 155D often tipped with between 75A and 77C.

The flowers, like the flowers of the parent, have no apparent fragrance.

REPRODUCTIVE ORGANS

There are 6 stamens, near 20B in color. The three-celled ovary is sessile and ovoid to subglabose in shape. Capsules are ovoid to oblong in shape and loculicidally dehiscent.

FOLIAGE

The numerous radical leaves are ligulate in shape and near 1 foot is length. Apices are acute and the base is channeled. Leaf color is between 137A and 144A. The foliage has a strong garlic-like fragrance that intensifies when the tissue is bruised.

Leaf count appears similar to the parent plant, that is, six to ten leaves per individual plant.

CULTIVATION

The new variety is particularly suitable for growing and substantially frost-free areas and may be grown as house plants or in large containers in glass houses. They are also grown in herb gardens or at the base of walls. Well-drained soils in full sun are preferred and 'Pertaylor' will tolerate slightly below freezing temperatures. However, it is preferred to maintain a minimum winter temperature of about 40° F.

CORM-LIKE RHIZOME

The individual plant divides and becomes two or more plants and this process continues as the clump of individual plants increases geometrically in number as the size of the clump increases in diameter. When the plant is planted as a bedding plant it spreads as a consequence of the division of the individual plants which increases the number of plants in the clump.

I claim:

1. A new and distinct variety of *Tulbaghia violacea* suitable for garden decoration, producing flowers of near white coloration, substantially as illustrated and described.

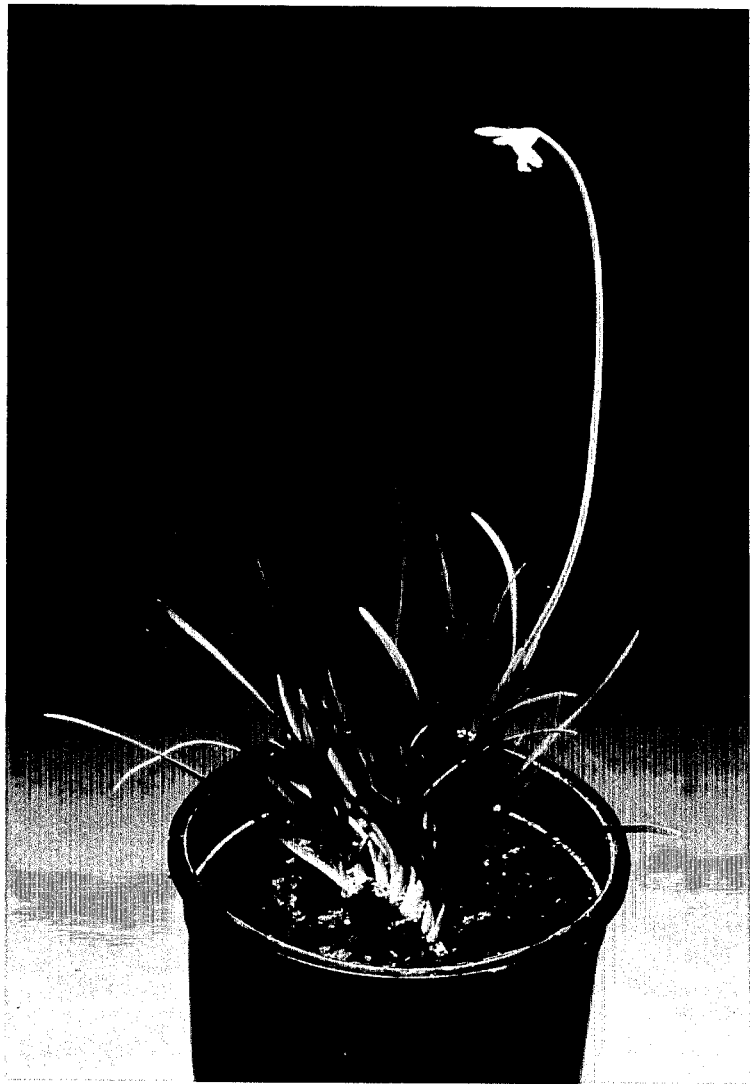

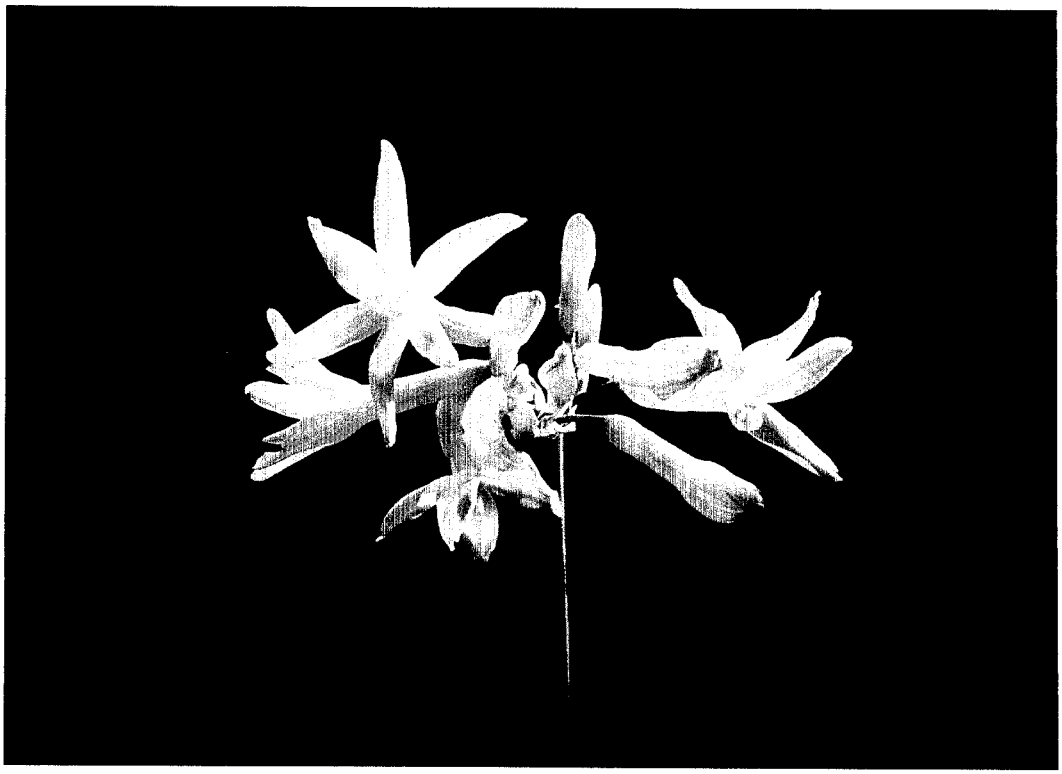

* * * * *